United States Patent [19]

Yamamoto et al.

[11] Patent Number: 5,663,365

[45] Date of Patent: Sep. 2, 1997

[54] PROCESS FOR THE PREPARATION OF PYRAZOLONES

[75] Inventors: Yasuo Yamamoto; Naoki Shirakawa; Shinichi Takano; Yoshio Kawai, all of Niigata, Japan

[73] Assignee: Japan Hydrazine Co., Ltd., Tokyo, Japan

[21] Appl. No.: 739,695

[22] Filed: Oct. 29, 1996

[51] Int. Cl.$^6$ .................. C07D 231/20; C07D 231/22
[52] U.S. Cl. .................. 548/366.1; 548/371.1
[58] Field of Search .................. 548/366.1, 371.1

[56] References Cited

PUBLICATIONS

Wiley et al. "Pyrazolones, Pyrazolidenes, and Derivatives" (1964) p. 10.

*Primary Examiner*—Robert W. Ramsuer
*Attorney, Agent, or Firm*—Robbins, Berliner & Carson, LLP

[57] ABSTRACT

A process for the preparation of pyrazolone derivatives represented by the general formula

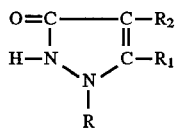

wherein R is a hydrogen atom, an alkyl group, an allyl group, an aryl group or an aralkyl group, and $R_1$ and $R_2$ are, respectively, a hydrogen atom, an alkyl group or a phenyl group which may have a substituent, comprising reacting a 2,3-dihalocarboxylic acid derivative or a 2-haloacrylic acid derivative with a hydrazine derivative. A pyrazolone or 1-substituted-3-pyrazolones useful as intermediate starting materials for the synthesis of agricultural chemicals, medicine and chemical compounds can be easily and cheaply prepared from widely used industrial starting materials.

7 Claims, No Drawings

PROCESS FOR THE PREPARATION OF PYRAZOLONES

BACKGROUND OF THE INVENTION

1. Field of the Invention

The present invention relates to a process for the preparation of pyrazolone derivatives that are useful as intermediate starting materials for synthesizing agricultural chemicals, medicine and chemical compounds.

2. Prior Art

The following methods have heretofore been known for obtaining a pyrazolone or 1-substituted-3-pyrazolones.

(1) A method of reacting an α- or an α, β-ester-substituted acetylene with a hydrazine compound or a hydrazone compound (CA 75:110227, CA 81:13426).

(2) A method of reacting a β-keto-acid ester with a hydrazine compound (CA 105:42788, Yakugakushi 60, 45, 1940).

(3) A method of reacting a β-chlorolactic acid ester with a hydrazine (Chem. Ber 27 407, 1894).

(4) A method of treating a 3-(N-phenylhydrazino) propionitrile with an alcoholic alkali (Boll Sci. Fac. Chim. Ind. Bolongna 11 78, 1953).

(5) A method of subjecting a corresponding pyrazolidone derivative to a treatment such as oxidation (Chem. Ber 29 519, 1896).

(6) A method of decarboxylating a carboxylate of a corresponding pyrazolone (Chem. Ber 40, 1021, 1907).

According to the above-mentioned methods (1) to (4), however, the starting materials are not usually easily available or are expensive. According to the above-mentioned methods (5) and (6), a step of cyclization reaction is necessary for synthesizing starting materials resulting in a substantial increase in the number of the steps.

As described above, the prior art for synthesizing pyrazolone derivatives is quite unsatisfactory as an industrial process since the starting materials are not easily available or are expensive, or the operations are cumbersome.

SUMMARY OF THE INVENTION

The present invention is to provide a method of cheaply and easily preparing a pyrazolone or 1-substituted-3-pyrazolones from widely used starting materials that are easily available and are easy to handle.

Through keen study, the present inventors have discovered the fact that a pyrazolone or 1-substituted-3-pyrazolones can be easily formed by reacting 2,3-dichlorocarboxylic acid esters, 2,3-dichlorocarboxylic acid amides, 2-chloroacrylic acid esters or 2-chloroacrylic acid amides with a hydrazine or mono-substituted hydrazines, and have arrived at the present invention.

According to the present invention, there is provided a process for the preparation of pyrazolone derivatives represented by the general formula (4),

  (4)

wherein R is a hydrogen atom, an alkyl group, an allyl group, an aryl group or an aralkyl group, and $R_1$ and $R_2$ are, respectively, a hydrogen atom, an alkyl group or a phenyl group which may have a substituent, comprising reacting 2,3-dihalocarboxylic acid derivatives represented by the following general formula (1), $$CHR_1X—CR_2X—CO—Z \quad (1)$$

wherein $R_1$ and $R_2$ have the meanings as described above, X is a halogen atom, and Z is a group —$OR_3$ ($R_3$ is a lower alkyl group) or a group —$NR_4R_5$ ($R_4$ and $R_5$ are, respectively, a hydrogen atom or an alkyl group), or 2-haloacrylic acid derivatives of the following general formula (2), $$CHR_1=CX—CO—Z \quad (2)$$

wherein $R_1$, X and Z have the meanings as described above, with hydrazine derivatives represented by the following general formula (3), $$R—HNNH_2 \quad (3)$$

wherein R has the meaning as described above.

The reaction in the process of the present invention is based upon the condensation and cyclization of 2,3-dihalocarboxylic acid derivatives or 2-haloacrylic acid derivatives with hydrazine derivatives as represented by the following reaction formula (5),

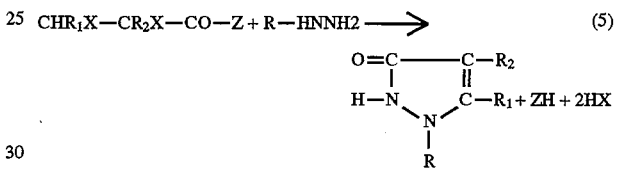  (5)

or the reaction formula (6),

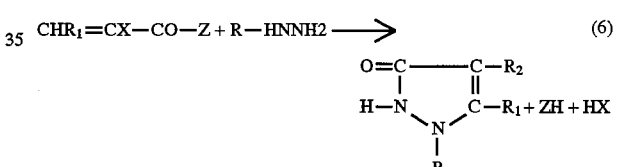  (6)

to form pyrazolone derivatives. During the condensation, there take place dehydrohalogenation, removal of alcohol in the case of ester and delamination in the case of amide. In the 2,3-dihaloca rboxylic acid derivatives, a double bond may take place due to the dehydrohalogenation in the molecules.

The condensation-cyclization reaction easily proceeds in the presence of an alkali which is a dehydrohalogenating agent, and the yield of the object product reaches 80 mol % or higher excluding some exceptions as will be described later in Examples. The melting points of the products are nearly in agreement with those described in the literatures and giving an advantage of high purity. Thus, according to the present invention, useful pyrazolone or 1-substituted-3-pyrazolones are easily prepared from the widely used starting materials that are cheaply available as described below.

That is, 2,3-dichlorocarboxylic acid esters which are the starting materials of the present invention can be synthesized in high yields by adding chlorine to α, β-unsaturated carboxylic acid esters which are usually easily available. For example, a desired methyl 2,3-dichloropropionate of a high purity can be prepared maintaining a yield of 70 to 90% by blowing a chlorine gas into a solution of carbon tetrachloride of methyl acrylate at 0° to 50° C. followed by distillation.

Furthermore, 2,3-dichlorocarboxylic acid amides which are the starting materials of the present invention can be easily synthesized by adding chlorine to α, β-unsaturated carbonitriles which are usually easily available followed by hydration. For example, a 2,3-dichloropropionic acid amide can be prepared by adding chlorine to an acrylonitrile followed by hydrolysis (CA 92:75870).

It has been known that 2-chloroacrylic acid esters which are the starting materials of the present invention can be prepared by treating 2,3-dichlorocarboxylic acid esters with an alkali salt (CA 16942, 1959, U.S. Pat. No. 2,476,528, 1945, U.S. Pat. No. 2,870,193, 1957).

It has been known that 2-chloroacrylic acid amides which are the starting materials of the present invention can be prepared by treating 2,3-dichlorocarboxylic acid-amides with an alkali salt (CA 102:78346, CA 103:71015, CA 76:58820).

DETAILED DESCRIPTION OF THE INVENTION

The 2,3-dihalocarboxylic acid derivatives which are the starting materials of the present invention are expressed by the above-mentioned general formula (1), wherein $R_1$ and $R_2$ are, respectively, a hydrogen atom, an alkyl group or a phenyl group that may have a substituent. Preferred examples of the alkyl group include lower alkyl groups having not more than 4 carbon atoms such as methyl, ethyl, propyl, isopropyl, butyl, isobutyl and tertiary butyl. The phenyl group may not be substituted or may have a substituent that does not take part in the reaction. Examples of the substituent may include the above-mentioned lower alkyl group, lower alkoxyl group, and halogen atom. X which is a halogen atom may be a chlorine atom, a bromine atom or an iodine atom. Among them, however, the chlorine atom is preferred. The following description chiefly deals with the case of the chlorine atom, to which only, however, the present invention is in no way limited. Z is a group —$OR_3$ ($R_3$ is a lower alkyl group) or a group —$NR_4R_5$ ($R_4$ and $R_5$ are respectively a hydrogen atom or an alkyl group) which corresponds to an ester or an amide.

Generally, the 2,3-dichlorocarboxylic acid esters which are the starting materials of the present invention are prepared by adding chlorine to α, β-unsaturated carboxylic acid esters, but can further be prepared by various methods that have been widely known without being limited thereto only. Though higher purity is desired, it is also allowable even if the starting materials contain by-products and solvent in the step of synthesis.

Some of concrete examples of the 2,3-dichlorocarboxylic acid esters will be methyl 2,3-dichloropropionate, ethyl 2,3-dichloropropionate, propyl 2,3-dichloropropionate, isopropyl 2,3-dichloropropionate, butyl 2,3-dichloropropionate, isobutyl 2,3-dichloropropionate, tertiary butyl 2,3-dichloropropionate, methyl 2,3-dichlorobutyrate, ethyl 2,3-dichlorobutyrate, methyl 2,3-dichloroisobutyrate, ethyl 2,3-dichloroisobutyrate, methyl 2,3-dichloro-3-phenylpropionate and ethyl 2,3-dichloro-3-phenylpropionate.

Generally, the 2,3-dichlorocarboxylic acid amides which are the starting materials of the present invention can be prepared by hydrating a chlorine adduct of α, β-unsaturated carbonitriles, but can be further prepared by various methods which have been widely known without being necessarily limited thereto only. Though higher purity is desired, it is also allowable even if the starting materials contain by-products and solvent in the step of synthesis.

Some of concrete examples of the 2,3-dichlorocarboxylic acid amides will be 2,3-dichloropropionic acid amide, 2,3-dichloropropionic acid-N-methylamide, 2,3-dichloropropionic acid-N-dimethylamide, 2,3-dichloropropionic acid-N-ethylamide, 2,3-dichloropropionic acid-N-diethylamide, 2,3-dichloropropionic acid-N-propylamide, 2,3-dichloropropionic acid-N-dipropylamide, 2,3-dichloropropionic acid-N-isopropylamide, 2,3-dichloropropionic acid-N-diisopropylamide, 2,3-dichloropropionic acid-N-butylamide, 2,3-dichloropropionic acid-N-dibutylamide, 2,3-dichloropropionic acid-N-isobutylamide, 2,3-dichloropropionic acid-N-diisobutylamide, 2,3-dichloropropionic acid-N-tertiary butylamide, 2,3-dichloropropionic acid-N-methyl ethylamide, 2,3-dichloromethyl-propionic acid amides, and 2,3-dichloro-3-phenylpropionic acid amides.

It has been known that the 2,3-chloroacrylic acid esters which are the starting materials of the present invention can be prepared by treating the 2,3-dichlorocarboxylic acid esters with an alkali salt, but can be further prepared by various methods which have been widely known without being necessarily limited thereto only. Though higher purity is desired, it is also allowable even if the starting materials contain by-products and solvent in the step of synthesis.

A typical compound of the 2-chloroacrylic acid esters is a methyl 2-chloroacrylate.

It has been known that the 2,3-chloroacrylic acid amides which are the starting materials of the present invention can be prepared by treating the 2,3-dichlorocarboxylic acid amides with an alkali salt, but can be further prepared by various methods which have been widely known without being necessarily limited thereto only. Though higher purity is desired, it is also allowable even if the starting materials contain by-products and solvent in the step of synthesis.

A typical compound of the 2-chloroacrylic acid amides is a 2-chloroacrylic acid amide.

The hydrazine derivatives used in the present invention are expressed by the above-mentioned general formula (3), wherein R is a hydrogen atom, an alkyl group, an allyl group, an aryl group or an aralkyl group. Examples of the aryl group include a phenyl group and a tolyl group, and examples of the aralkyl group include a benzyl group and a phenetyl group.

The hydrazine is usually a hydrazine hydrate, but may be a salt with an inorganic acid or a salt with an organic acid which easily reproduces hydrazine upon neutralization, or may be an aqueous solution thereof.

On the other hand, it is desired that the mono-substituted hydrazines are substantially in a pure form but may be a salt with an inorganic acid or a salt with an organic acid, or may be an aqueous solution thereof.

According to the present invention, it is desired that the hydrazine or mono-substituted hydrazines are used in an amount of from 0.5 to 6 mols per mol of another starting material, i.e., 2,3-dichlorocarboxylic acid esters, 2,3-dichlorocarboxylic acid amides, 2-chloroacrylic acid esters or 2-chloroacrylic acid amides.

The alkali used as a dehydrohalogenating agent for promoting the reaction of the present invention is sodium hydroxide, potassium hydroxide, sodium carbonate, potassium carbonate, or tertiary amine (e.g., trimethylamine, tributylamine, pyridine, etc.).

The hydrazine and mono-substituted hydrazines which are the starting materials also work as dehydrohalogenating agents.

The process of the present invention can be conducted either using or without using a solvent, but is desirably conducted by using a suitable solvent. Suitable examples of the solvent may include water, alcohol, ether, aromatic hydrocarbons, or a mixture solvent thereof. It is also allowable to use any other solvent provided it does not react with the starting materials. Representative examples of the solvent include water, methanol, ethanol, propanol, tetrahydrofuran, toluene and xylene.

The reaction according to the present invention can be carried out over a wide range of temperatures of usually from −10° C. up to a refluxing temperature of the solvent but is desirably carried out within a range of from 0° to 50 ° C. The reaction time is from 0.1 to 40 hours. When the reaction is carried out at 0° to 50° C., however, the reaction time is from 1 to 6 hours.

According to the present invention, the reaction can be carried out under atmospheric pressure, reduced pressure or elevated pressure. In industrially, however, it is advantageous to carry out the reaction under atmospheric pressure.

The process of the present invention can be carried out in a batchwise manner, a half-batchwise manner or in a flowing manner without any particular limitation.

There can be employed, for example, (1) a method in which one type of starting materials, i.e., hydrazine or mono-substituted hydrazines are dropwisely added to the solution of another type of starting materials, i.e., 2,3-dichlorocarboxylic acid esters, 2,3-dichlorocarboxylic Acid amides, 2-chloroacrylic acid esters or 2-chloroacrylic acid amides, and the temperature is suitably raised, (2) a method in which one type of starting materials, i.e., 2,3-dichlorocarboxylic acid esters, 2,3-dichlorocarboxylic acid amides, 2-chloroacrylic acid esters or 2-chloroacrylic acid amides are dropwisely added at normal temperature to another type of starting materials, i.e., hydrazine or mono-substituted hydrazines, and the temperature is suitably raised, or (3) a method in which one type of starting materials, i.e., 2,3-dichlorocarboxylic acid esters, 2,3-dichlorocarboxylic acid amides, 2-chloroacrylic acid esters or 2-chloroacrylic acid amides and another type of starting materials, i.e., hydrazine or mono-substituted hydrazines are simultaneously and dropwisely added at a predetermined temperature.

According to the present invention, the desired pyrazolones can be taken out from the reaction product by any one of the generally employed separation methods such as distillation, extraction or recrystallization or by a combination thereof without being necessarily limited to only one of them.

The invention will now be concretely described by way of Examples to which only, however, the invention is in no way limited.

EXAMPLE 1

Synthesis of a Pyrazolone 10.0 Grams (67 mmols) of a 2,3-dichloropropionic acid amide and 100 g of a tetrahydrofuran were fed into a 200-ml four neck flask, followed by the dropwise addition of 10.1 g (202mmols) of a hydrated hydrazine over a period of 20 minutes in a water bath maintained at 15° C. with stirring. The temperature was then raised to 50° C., and the reaction was finished after stirred for one hour. 100 Grams of the tetrahydrofuran was added to the reaction product that was obtained by condensing and drying the reaction solution, and the mixture was stirred at room temperature. After insoluble matters were separated by filtration, the tetrahydrofuran solution of the product was analyzed by gas chromatography to find that a pyrazolone was contained in an amount of 5.3 g. The yield of the pyrazolone was 94 mol % on the basis of the 2,3-dichloropropionic acid amide. The tetrahydrofuran solution of the above product was condensed and dried again, and was recrystallized with water to obtain white crystals of the pyrazolone, m.p. 162° to 164° C. (165° C. according to the literature).

EXAMPLE 2

Synthesis of a 1-methyl-3-pyrazolone 20.0 Grams (98%, 430 mmols) of a monomethyl hydrazine and 80 g of methanol were fed into a 200-ml four neck flask, followed by the dropwise addition of 22.5 g (99%, 142 mmols) of a methyl 2,3-dichloropropionate over a period of 30 minutes in a water bath maintained at 15° C. with stirring. The temperature was then raised to 50° C., and the reaction was finished after stirred for one hour. 136 Grams of the tetrahydrofuran was added to the reaction product that was obtained by condensing and drying the reaction solution, and the mixture was stirred at room temperature. After insoluble matters were separated by filtration, the tetrahydrofuran solution of the product was analyzed by gas chromatography to find that a 1-methyl-3-pyrazolone was contained in an amount of 12.9 g. The yield of the 1-methyl-3-pyrazolone was 92 mol % on the basis of the methyl 2,3-dichloropropionate. The tetrahydrofuran solution of the above product was condensed and dried again, and was recrystallized with water and then with acetonitrile to obtain white crystals of the 1-methyl-3-pyrazolone, m.p. 126 to 128° C. (127° C. according to the literature).

EXAMPLE 3

Synthesis of a 1-isopropyl-3-pyrazolone 18.6 Grams (95%, 238 mmols) of a monoisopropyl hydrazine and 90 g of a tetrahydrofuran were fed into a 200-ml four neck flask, followed by the dropwise addition of 12.6 g (99%, 79 mmols) of a methyl 2,3-dichloropropionate over a period of 6 minutes in a water bath with stirring. The temperature was then raised to 50° C., and the reaction was finished after stirred for one hour. Insoluble matters were separated by filtration from the cooled reaction solution. The reaction solution was analyzed by gas chromatography to find that a 1-isopropyl-3-pyrazolone was obtained in a yield of 62 mol % on the basis of the methyl 2,3-dichloropropionate. The reaction solution was condensed and dried, and was recrystallized with acetonitrile to obtain white crystals of the 1-isopropyl-3-pyrazolone, m.p. 131° to 132° C. (131° to 132° C. according to the literature).

EXAMPLE 4

Synthesis of a 1-butyl-3-pyrazolone 28.2 Grams (98%, 303 mmols) of a monobutyl hydrazine was reacted with 16.4 g (97%, 101 mmols) of a methyl 2,3-dichloropropionate in the same manner as in Example 3. The reaction solution was condensed and dried to obtain an oily product to which was, then, added 150 g of water, and the mixture was stirred at room temperature. The formed crude crystals were filtered and dried to obtain 11.8 g of crude crystals which were then analyzed by gas chromatography to find that a 1-butyl-3-pyrazolone was contained in an amount of 11.6 g. The yield of the 1-butyl-3-pyrazolone was 82 mol % on the bases of the methyl 2,3-dichloropropionate.

The crude crystals were recrystallized with acetonitrile to obtain white crystals of the 1-butyl-3-pyrazolone, m.p. 57° to 59° C.

EXAMPLE 5

Synthesis of a 1-methyl-5-phenyl-3-pyrazolone 20.0 Grams (99%, 85 mmols) of a methyl 2,3-dichloro-3-phenylpropionate and 200 g of a tetrahydrofuran were fed into a 300-ml four neck flask, followed by the dropwise addition of 17.2 g (98%, 366 mmols) of a monomethyl hydrazine over a period of 10 minutes at room temperature with stirring. Then, the temperature was raised to 50° C. and the reaction was finished after stirred for 3 hours. 440 Grams of water was added to the reaction product obtained by condensing and drying the reaction solution, and the mixture was stirred at room temperature. The formed crude crystals were filtered and dried and were analyzed by gas chromatography to find that a 1-methyl-5-phenyl-3-pyrazolone was obtained in a yield of 62 mol % on the basis of the methyl 2,3-dichloro-3-phenylpropionate. The crude crystals were recrystallized with acetonitrile to obtain white crystals of the 1-methyl-5-phenyl-3-pyrazolone, m.p. 164° to 165° C. (160° to 165° C. according to the literature).

EXAMPLE 6

Synthesis of a methyl 2-chloroacrylate 15.7 Grams (99%, 100 mmols) of a methyl 2,3-dichloropropionate and 50 g of a tetrahydrofuran were fed into a 200-ml four neck flask, followed by the dropwise addition of 10.1 g (100 mmol) of a triethylamine over a period of 40 minutes at room temperature with stirring. The reaction was finished after stirred at room temperature for four hours. After the formed precipitate was removed by filtration, the solvent was distilled from the reaction solution under reduced pressure. Then, through the reduced pressure distillation under 50 mmHg, there was obtained 11.2 g of a methyl 2-chloroacrylate as a fraction of 45° to 60° C. The yield of the methyl 2-chloroacrylate was 90 mol % on the basis of the methyl 2,3-dichloropropionate, and the purity was 97% as determined by gas chromatography.

Synthesis of a 1-ethyl-3-pyrazolone 3.7Grams (30 mmols) of a methyl 2-chloroacrylate and 19 g of a tetrahydrofuran were fed into a 50 ml four neck flask, followed by the dropwise addition of 3.9 g (92%, 60 mmols) of a monoethyl hydrazine over a period of 60 minutes at room temperature with stirring. The reaction was finished after the mixture was stirred at room temperature for 3 hours. The reaction solution was separated into two layers. The solution of the upper layer was analyzed by gas chromatography to find that a 1-ethyl-3-pyrazolone was contained in an amount of 2.9 g. The yield of the 1-ethyl-3-pyrazolone was 86 mol % on the basis of the methyl 2-chloroacrylate. The solution of the upper layer was condensed and dried, and was recrystallized with water to obtain white crystals of the 1-ethyl-3-pyrazolone, m.p. 94° to 95° C. (92° to 94° C. according to the literature).

EXAMPLE 7

Synthesis of a 2chloroacrylic acid amide 14.2 Grams (100 mmol) of a 2,3-dichloropropionic acid amide and 200 g of a tetrahydrofurane were fed into a 500-ml four neck flask, followed by the dropwise addition of 10.1 g (100 mmol) of a triethylamine over a period of 30 minutes at room temperature with stirring. The temperature was then raised to 40° C., and the reaction was finished after stirred for 20 hours. The formed precipitate was removed by filtration to obtain a solution of a 2-chloroacrylic acid amide.

Synthesis of a 1-ethyl-3-pyrazolone

A solution of a 2-chloroacrylic acid amide was fed to a 500-ml four neck flask followed by the dropwise addition of 13.0 g (92%, 200 mmol) of a monoethyl hydrazine over a period of 30 minutes at room temperature with stirring. Then, the temperature was raised to 40° C., and the reaction was finished after stirred for 4 hours. The reaction solution was analyzed by gas chromatography to find that a 1-ethyl-3-pyrazolone was contained in an amount of 9.0 g. The yield of the 1-ethyl-3-pyrazolone was 80mol % on the basis of the 2,3-dichloropropionic acid amide which was the starting material.

The reaction solution was condensed and dried to obtain a product which was then recrystallized with water to obtain white crystals of the 1ethyl 3-pyrazolone, m.p. 92° to 93° C. (92° to 94° C. according to the literature).

According to the present invention, a pyrazolone or 1-substituted-3-pyrazolones which are useful intermediate starting materials for the synthesis of agricultural chemicals, medicine and other chemical compounds, can be easily and cheaply prepared from widely used industrial starting materials.

We claim:

1. A process for the preparation of pyrazolone derivatives represented by the general formula (4), $$O=C-C-R_2 \atop H-N\diagdown_N\diagup C-R_1 \atop \underset{R}{|}$$ (4)

wherein R is a hydrogen atom, an alkyl group, an allyl group, an aryl group or an aralkyl group, and $R_1$ and $R_2$ are, respectively, a hydrogen atom, an alkyl group or a phenyl group which may have a substituent, comprising reacting 2,3-dihalocarboxylic acid derivatives represented by the following general formula (1), $$CHR_1X—CR_2X—CO—Z$$ (1)

wherein $R_1$ and $R_2$ have the meanings as described above, X is a halogen atom, and Z is a group —$OR_3$ ($R_3$ is a lower alkyl group) or a group —$NR_4R_5$ ($R_4$ and $R_5$ are, respectively, a hydrogen atom or an alkyl group), or 2-haloacrylic acid derivatives of the following general formula (2), $$CHR_1=CX—CO—Z$$ (2)

wherein $R_1$, X and Z have the meanings as described above, with hydrazine derivatives represented by the following general formula (3), $$R—HNNH_2$$ (3)

wherein R has the meaning as described above.

2. A process according to claim 1, wherein the 2,3-dihalocarboxylic acid derivative is a 2,3-dichlorocarboxylic acid ester.

3. A process according to claim 1, wherein the 2,3-dihalocarboxylic acid derivative is a 2,3-dichlorocarboxylic acid amide.

4. A process according to claim 1, wherein the 2-haloacrylic acid derivative is a 2-chloroacrylic acid ester.

5. A process according to claim 1, wherein the 2-haloacrylic acid derivative is a 2-chloroacrylic acid amide.

6. A process according to claim 1, wherein the hydrazine derivative is used in an amount of from 0.5 to 6 mols per mol of the 2,3-dihalocarboxylic acid derivative or the 2-haloacrylic acid derivative.

7. A process according to claim 1, wherein the reaction is carried out at a temperature of from 0° to 50° C.

* * * * *